(12) United States Patent
Mohiuddin et al.

(10) Patent No.: US 8,771,289 B2
(45) Date of Patent: Jul. 8, 2014

(54) THROMBUS REMOVAL DEVICE AND SYSTEM

(75) Inventors: Khader Mohiuddin, Medina, MN (US); Robert F. Wilson, Roseville, MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 430 days.

(21) Appl. No.: 12/643,499

(22) Filed: Dec. 21, 2009

(65) Prior Publication Data
US 2011/0152823 A1    Jun. 23, 2011

(51) Int. Cl.
*A61B 17/22*     (2006.01)
(52) U.S. Cl.
USPC .......................... 606/127; 606/200
(58) Field of Classification Search
USPC .......... 600/585, 125, 124, 106, 104; 606/110–115, 127, 128, 194, 200, 198, 606/192, 170, 159; 604/523, 104, 528, 107, 604/22, 103.01, 118, 124, 125, 131, 134, 604/173, 171, 176, 192, 164.08, 164.09, 604/164.13, 35, 508, 509, 507
See application file for complete search history.

(56) References Cited

U.S. PATENT DOCUMENTS

| | | | |
|---|---|---|---|
| 4,771,782 A | 9/1988 | Millar | |
| 4,850,358 A | 7/1989 | Millar | |
| 4,921,484 A * | 5/1990 | Hillstead | 604/104 |
| 4,928,693 A | 5/1990 | Goodin et al. | |
| 4,966,148 A | 10/1990 | Millar | |
| 4,991,590 A | 2/1991 | Shi | |
| 5,046,497 A | 9/1991 | Millar | |
| 5,178,159 A | 1/1993 | Christian | |
| 5,280,786 A | 1/1994 | Wlodarczyk et al. | |
| 5,395,311 A | 3/1995 | Andrews | |
| 5,439,445 A * | 8/1995 | Kontos | 604/103.1 |

(Continued)

FOREIGN PATENT DOCUMENTS

| | | |
|---|---|---|
| EP | 01419796 B1 | 3/2008 |
| JP | 2010-099215 | 5/2010 |
| WO | WO 96/07351 A1 | 3/1996 |

OTHER PUBLICATIONS

International Search Report of the International Searching Authority, International Application No. PCT/US2010/061516 mailed Feb. 11, 2011, 2 pages.

(Continued)

*Primary Examiner* — Kathleen Holwerda
*Assistant Examiner* — Jocelin Tanner
(74) *Attorney, Agent, or Firm* — Fredrikson & Byron, P.A.

(57) ABSTRACT

Devices and methods for removing a thrombus (clot) from a vascular structure of a living subject. An embodiment of a thrombus removal device comprises first and second annular members, the first annular member being adapted to slide over a guidewire placed in a vascular structure, the second annular member being coupled to the first annular member and having a suction flow path therethrough, the first annular member having an expandable mesh structure disposed at a distal portion thereof, the mesh structure being deployable to an expanded configuration by movement of an actuating element extending along the second annular member. An embodiment of a thrombus removal method comprises advancing the device to position the mesh structure downstream of the thrombus by sliding the first annular member over the guidewire, applying a suction force to the suction flow path of the second annular member, deploying the mesh structure, and retracting the device to cause the mesh structure to engage the thrombus.

34 Claims, 13 Drawing Sheets

(56) References Cited

U.S. PATENT DOCUMENTS

| | | | |
|---|---|---|---|
| 5,527,282 A * | 6/1996 | Segal | 604/104 |
| 5,533,957 A | 7/1996 | Aldea | |
| 5,597,377 A | 1/1997 | Aldea | |
| 5,715,827 A | 2/1998 | Corl et al. | |
| 5,782,797 A | 7/1998 | Schweich, Jr. et al. | |
| 5,827,304 A | 10/1998 | Hart | |
| 5,938,624 A | 8/1999 | Akerfeldt et al. | |
| 6,112,598 A | 9/2000 | Tenerz et al. | |
| 6,146,354 A | 11/2000 | Beil | |
| 6,166,806 A | 12/2000 | Tjin | |
| 6,167,763 B1 | 1/2001 | Tenerz et al. | |
| 6,192,568 B1 * | 2/2001 | Kafrawy et al. | 29/412 |
| 6,196,980 B1 | 3/2001 | Akerfeldt et al. | |
| 6,231,588 B1 * | 5/2001 | Zadno-Azizi | 606/200 |
| 6,248,083 B1 | 6/2001 | Smith et al. | |
| 6,615,667 B2 | 9/2003 | Smith | |
| 6,673,042 B1 * | 1/2004 | Samson et al. | 604/104 |
| 6,852,261 B2 | 2/2005 | Benjamin | |
| 6,868,736 B2 | 3/2005 | Sawatari et al. | |
| 6,875,193 B1 | 4/2005 | Bonnette et al. | |
| 6,976,965 B2 | 12/2005 | Corl et al. | |
| 7,134,994 B2 | 11/2006 | Alpert et al. | |
| 7,329,223 B1 | 2/2008 | Ainsworth et al. | |
| 7,524,319 B2 * | 4/2009 | Dubrul | 606/113 |
| 2001/0031981 A1 * | 10/2001 | Evans et al. | 606/200 |
| 2002/0058904 A1 | 5/2002 | Boock et al. | |
| 2002/0065507 A1 * | 5/2002 | Zadno-Azizi | 604/509 |
| 2003/0023230 A1 * | 1/2003 | Lewis et al. | 604/537 |
| 2003/0088213 A1 * | 5/2003 | Schweikert et al. | 604/177 |
| 2004/0147864 A1 * | 7/2004 | Lenker et al. | 604/4.01 |
| 2004/0168519 A1 | 9/2004 | Kalvensten et al. | |
| 2004/0236369 A1 | 11/2004 | Dubrul | |
| 2006/0133715 A1 | 6/2006 | Belleville et al. | |
| 2006/0161110 A1 * | 7/2006 | Lenker et al. | 604/183 |
| 2006/0229645 A1 * | 10/2006 | Bonnette et al. | 606/159 |
| 2006/0287667 A1 * | 12/2006 | Abela | 606/200 |
| 2007/0135832 A1 * | 6/2007 | Wholey et al. | 606/200 |
| 2007/0198051 A1 | 8/2007 | Clubb et al. | |
| 2007/0255145 A1 | 11/2007 | Smith et al. | |
| 2008/0119758 A1 | 5/2008 | Samuelsson et al. | |
| 2008/0262410 A1 | 10/2008 | Jenson et al. | |
| 2010/0234698 A1 | 9/2010 | Manstrom et al. | |
| 2010/0241008 A1 | 9/2010 | Belleville et al. | |

OTHER PUBLICATIONS

International Preliminary Report on Patentability, International Application No. PCT/US2010/061516 mailed Jul. 5, 2012, 8 pages.
Published Japanese Translation of PCT International Publication for Patent Application No. 2001-521779.
Published Japanese Translation of PCT International Publication for Patent Application No. 2007-527264.
Published Japanese Translation of PCT International Publication for Patent Application No. 2008-526378.

* cited by examiner

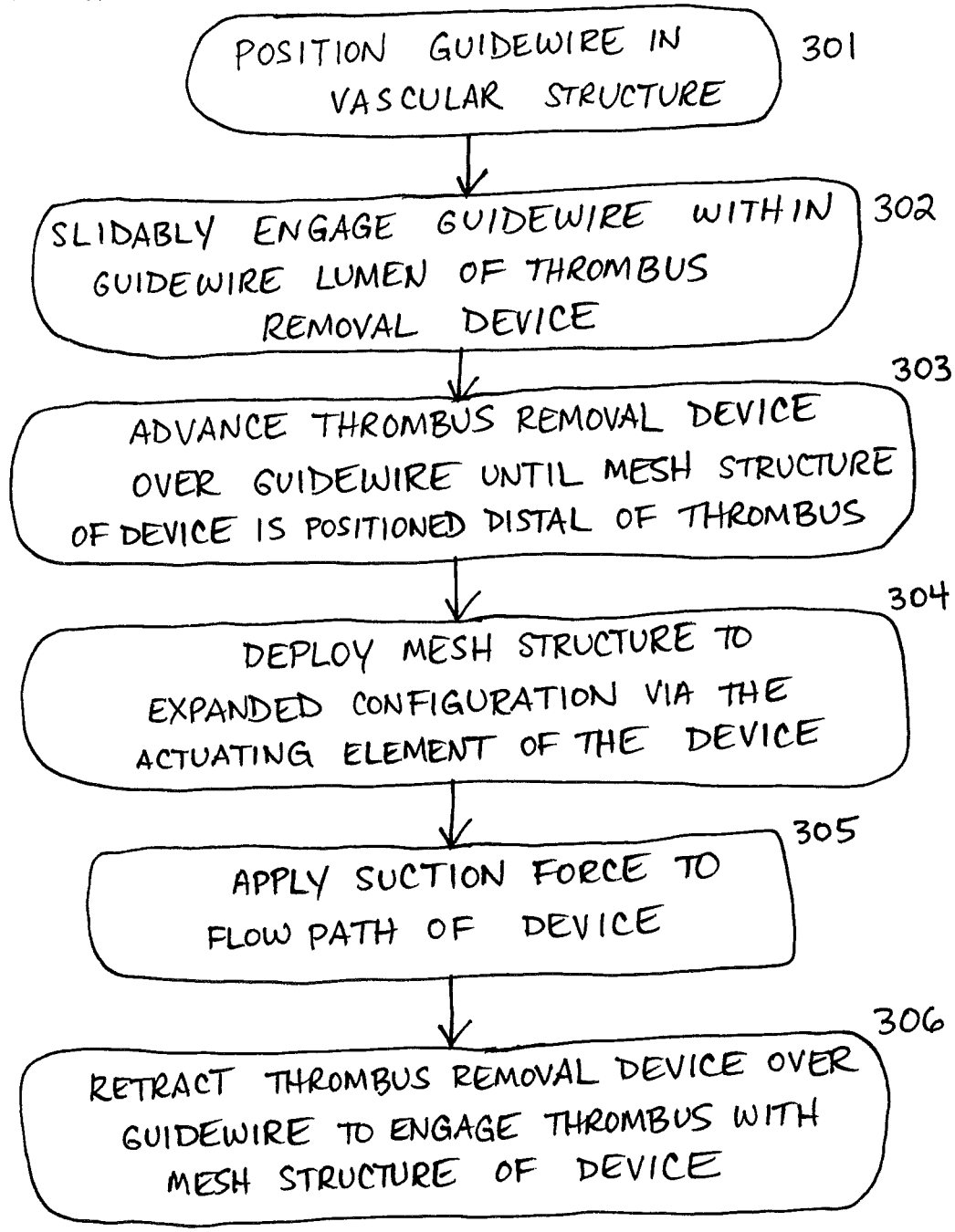

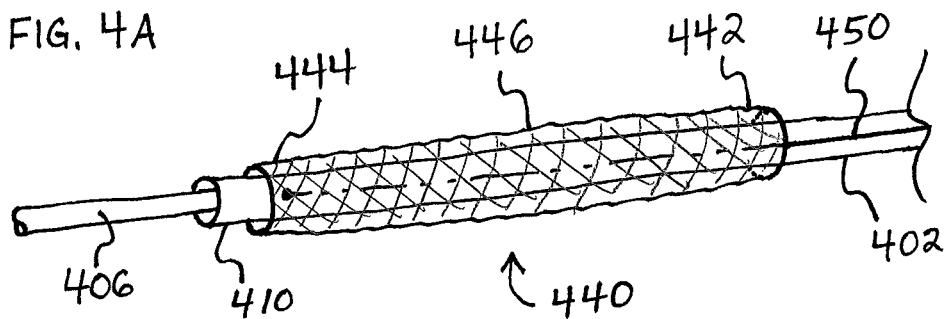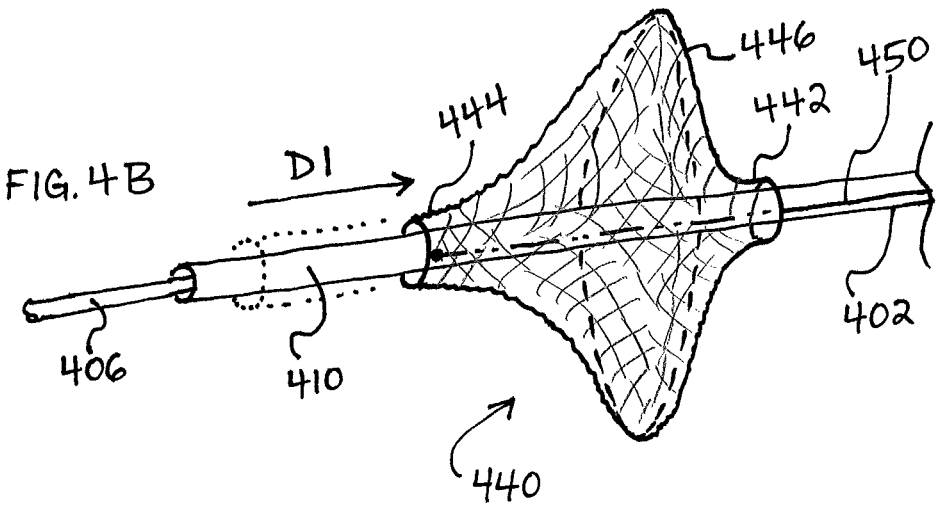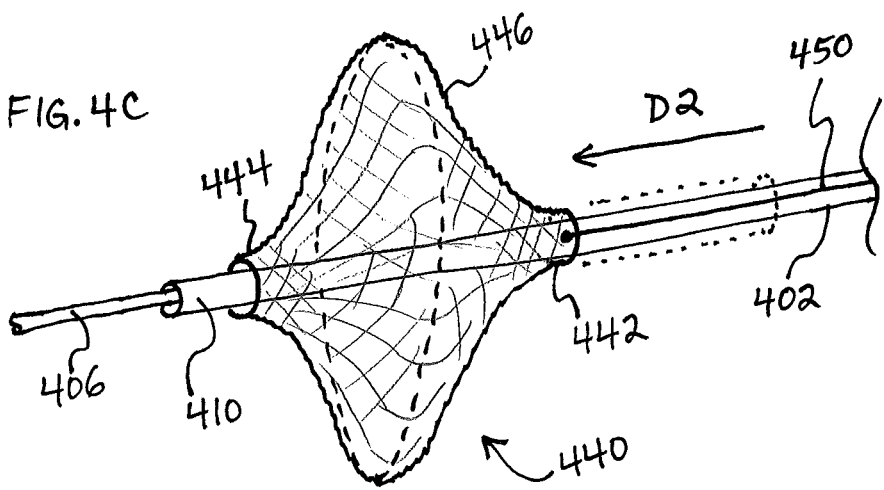

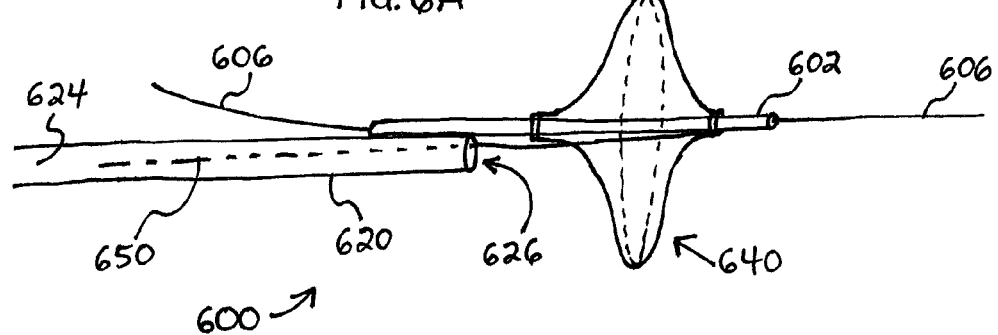
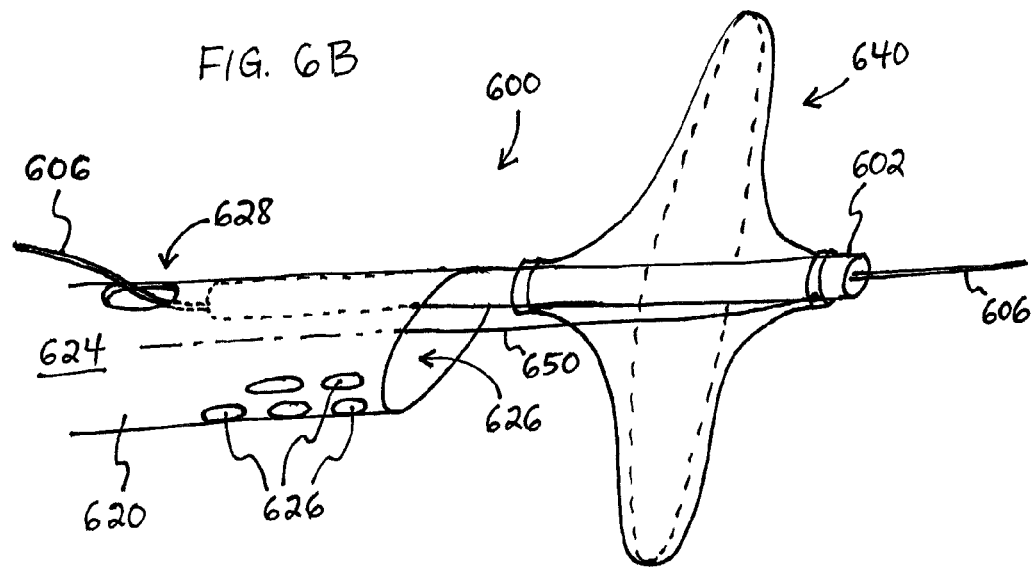

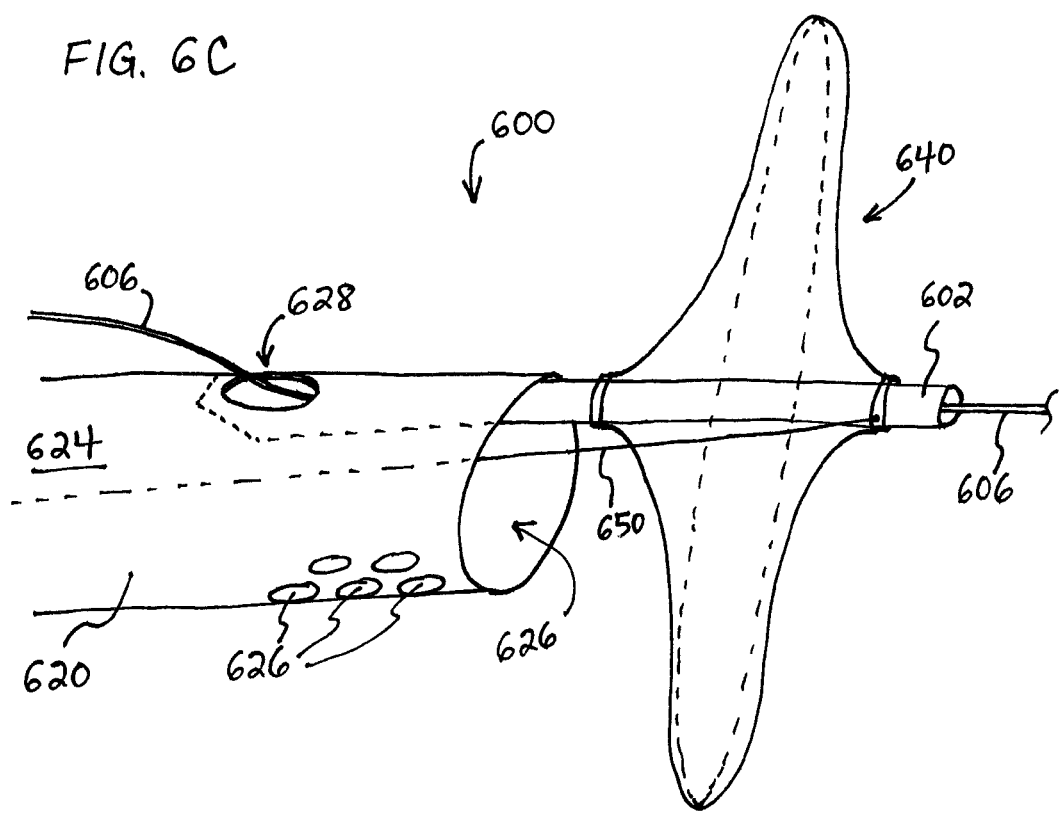

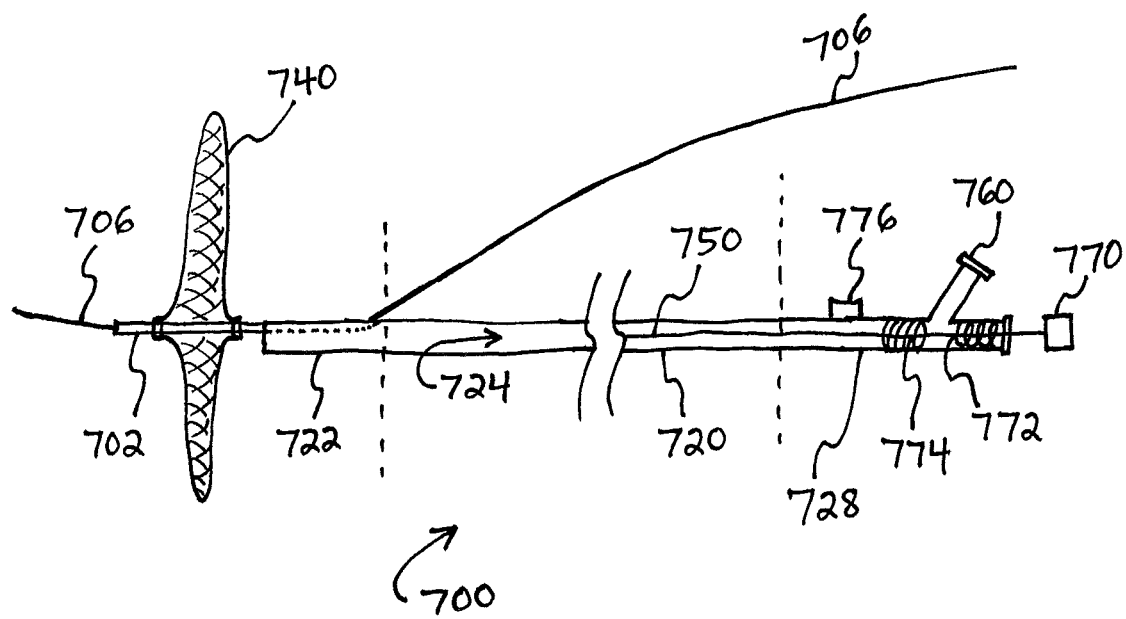

THROMBUS REMOVAL DEVICE AND SYSTEM

TECHNICAL FIELD

This application relates generally to the field of medical device technology and, more particularly, to devices and systems for removing a thrombus (clot) from a vascular structure of a living subject.

BACKGROUND

A blood clot that forms in a blood vessel and remains there is called a thrombus. If a thrombus becomes large enough, for example, it may obstruct the flow of blood through the vessel and may thereby cause damage or even death to surrounding tissue.

Current methods to treat thrombus include the use of thrombolytic drugs and/or mechanical thrombectomy devices. Thrombolytic drugs may require multiple treatments to be effective, and they may only partially remove the clot. Thrombolytic drugs may also require significant time to take effect, which may become costly in intensive care settings. Thrombolytic drugs may also cause bleeding.

Current thrombectomy devices are typically difficult to use in small blood vessels (e.g., coronary vessels) due to the relatively large size of such devices. Currently available thrombectomy devices also tend to be relatively expensive. It is therefore desirable to provide a device suitable for removing a thrombus from small blood vessels (e.g., coronary arteries). Such a device would preferably be capable of providing distal embolism protection while maintaining downstream blood flow, and would preferably be cost-effective.

SUMMARY

In certain embodiments, a thrombus removal device comprises first and second annular members, the first annular member being adapted to slide over a guidewire placed in a vascular structure, the second annular member being coupled to the first annular member and having a suction (or aspiration) flow path therethrough. The first annular member has an expandable mesh structure disposed at a distal portion thereof. The mesh structure is deployable to an expanded configuration by movement of an actuating element extending along the second annular member.

In certain embodiments, a thrombus removal method comprises advancing the thrombus removal device to position the mesh structure downstream of the thrombus by sliding the first annular member over the guidewire. A suction force may be applied to the suction flow path of the second annular member. The mesh structure is deployed via the actuating element, and the device is retracted to cause the mesh structure to engage the thrombus. Portions of the thrombus may be captured by the mesh structure and removed from the vascular structure. In addition, or alternatively, portions of the thrombus may become dislodged and may be removed from the vascular structure via the suction flow path of the second annular member. In addition, or alternatively, portions of the thrombus may be removed from the vascular structure by a "wiping" action of the mesh structure along a wall of the vascular structure.

BRIEF DESCRIPTION OF THE DRAWINGS

FIGS. 3(a) and 3(b) are flowcharts showing the steps in two exemplary methods for removing a thrombus from a vascular structure according to some embodiments;

FIGS. 4(a) through 4(f) are partial perspective views of a flexible mesh structure of a thrombus removal device, according to various embodiments;

FIGS. 6(a) through 6(d) are side views showing possible alternative coupling arrangements of the first and second annular members of a thrombus removal device, according to certain embodiments; and FIG. 7 is a side view of a thrombus removal device with a proximal portion adapted to couple the device to a suction (or aspiration) source and/or an actuating mechanism according to certain embodiments.

DETAILED DESCRIPTION

The following detailed description should be read with reference to the accompanying drawings, in which like numerals denote like elements. The drawings, which are not necessarily to scale, depict selected embodiments of the invention as claimed—other possible embodiments may become readily apparent to those of ordinary skill in the art with the benefit of these teachings. Thus, the embodiments shown in the accompanying drawings and described below are provided for illustrative purposes, and are not intended to limit the scope of the present disclosure as defined in the claims appended hereto.

Figure 1:
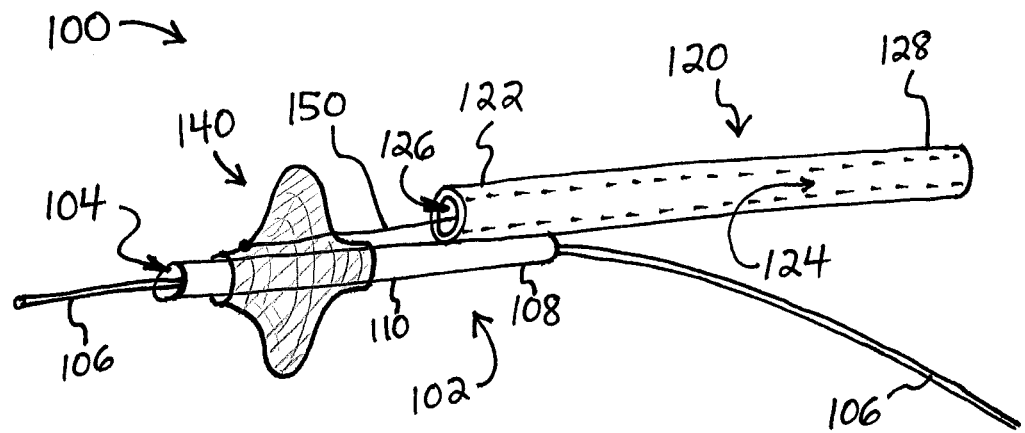
FIG. 1 is a side view of a device for removing a thrombus from a vascular structure, according to an embodiment.

FIG. 1 is a side perspective view of a device 100 for removing a thrombus from a vascular structure, according to an embodiment. Device 100, as shown in FIG. 1, comprises a first annular member 102 having a guidewire lumen 104 for slidably receiving a guidewire 106. Guidewire 106 may be any medical guidewire. The selection of a particular guidewire by a physician may be affected, for example, by the physician's preference, or the vascular structure of interest, or some combination of these and other factors. The size (e.g., the diameter, length, etc.) and/or the stiffness of the guidewire selected may comprise guidewire characteristics that factor into the selection of a suitable guidewire for a particular procedure or a particular vascular structure of interest, for example.

The size (e.g., diameter) of guidewire lumen 104 is typically somewhat larger than the outer diameter of the guidewire 106. Guidewire lumen 104 may be of a size to allow for use with guidewires having a certain range of sizes. Thus, it is envisioned that device 100 could be made commercially having guidewire lumens available in a number of different sizes (e.g., small, medium, large, etc.) such that each size would be adapted to slidably receive a specific guidewire size, or a corresponding range of guidewire sizes. In certain preferred embodiments of the invention, the guidewire lumen 104 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.014, 0.018, 0.021, 0.025, 0.028, 0.032, 0.035, and 0.038 inches. Thus, in certain preferred embodiments of the invention, the guidewire lumen 104 may be sized appropriately to slide over a particular standard size medical guidewire. A device according to preferred embodiments of the invention may therefore be made available in a range of sizes corresponding to standard medical guidewire sizes.

One potential advantage of a device 100 according to certain embodiments of the invention is that it allows a physician to use the guidewire 106 of their choice. The physician may, for example, choose a particular guidewire 106 based on its unique flexing and torque characteristics for certain procedures. Device 100 according to various embodiments provides the physician with the ability to use whichever guidewire 106 is deemed best suited for the particular application.

With continued reference to FIG. 1, device 100 comprises a second annular member 120 coupled to the first annular member 102. The second annular member 120 is adapted to provide a suction (aspiration) flow path 124 from a suction (aspiration) port 126 in the distal portion 122 of the second annular member 120 to the proximal portion 128 of the second annular member 120. In the embodiment shown in FIG. 1, the distal portion 122 of the second annular member 120 is coupled to the proximal portion 108 of the first annular member 102.

In the embodiment of FIG. 1, device 100 further includes a flexible mesh structure 140 coupled to an outer surface of a distal portion 110 of the first annular member 102. Flexible mesh structure 140 is adapted to be deployed to an expanded configuration. In some embodiments, flexible mesh structure 140 is maintained in a substantially collapsed configuration while it is being positioned in the vascular structure of interest. In the substantially collapsed configuration, flexible mesh structure 140 may substantially conform to the outer surface of distal portion 110 of first annular member 102, for example.

Device 100 further comprises an actuating element 150. As shown in FIG. 1, actuating element 150 may be coupled to the flexible mesh structure 140. Actuating element 150 may extend from the mesh structure 140 to the proximal portion 128 of the second annular member 120. The actuating element 150 is adapted to cause the flexible mesh structure to deploy to an expanded configuration. The deployment of the mesh structure 140 to the expanded configuration may be accomplished by movement of the actuating element 150, according to some embodiments. Such movement might comprise longitudinal movement (e.g., proximal or distal movement) or rotational movement, for example. Alternately, the mesh structure 140 may be deployed to the expanded configuration in response to a signal communicated to the actuating element 150 (e.g., via an electrical signal or thermal signal). In the specific embodiment shown in FIG. 1, the actuating element 150 comprises an actuating wire or rod that is at least partially housed and/or guided within suction flow path 124. In some embodiments, an actuating lumen (not shown in FIG. 1) may be incorporated as part of the second annular member 120 such that the actuating element 150 is housed and/or guided separately from the suction flow path 124.

Figure 2A:
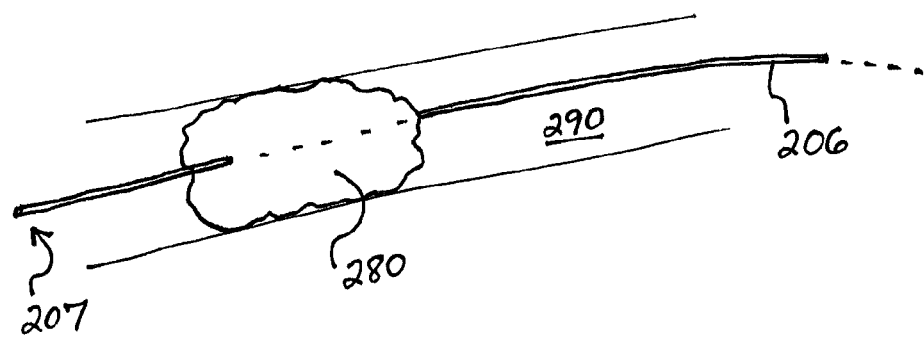
FIGS. 2(a) through 2(e) illustrate a method of removing a thrombus from a vascular structure using a thrombus removal device according to an embodiment.

FIGS. 2(a) through 2(e) are a series of idealized side views illustrating a method of removing a thrombus from a vascular structure of interest. FIG. 2(a) shows a thrombus (or clot) 280 located in a vascular structure of interest 290. A method of removing a thrombus 280 from a vascular structure of interest may comprise positioning a guidewire 206 in the vascular structure 290 such that a distal end 207 of the guidewire 206 is positioned distally of the thrombus 280.

Figure 2B:
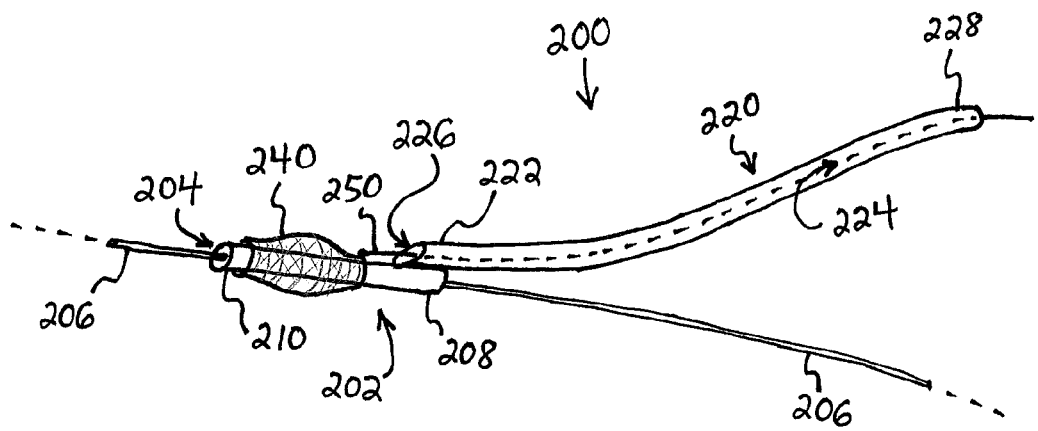

FIG. 2(b) shows thrombus removal device 200 slidably engaging guidewire 206 within guidewire lumen 204 of device 200. Device 200 comprises a first annular member 202 having a guidewire lumen 204 extending therethrough. Device 200 further comprises a second annular member 220 coupled to the first annular member 202. The second annular member 220 includes a suction flow path 224 from a suction port 226 in a distal portion 222 of the second annular member 220 to a proximal portion 228 of the second annular member 220.

As shown in FIG. 2(b), the distal portion 222 of the second annular member 220 is coupled to a proximal portion 208 of the first annular member 202. Also shown in FIG. 2(b), the first annular member 202 is coupled to the second annular member 220 in a "side-by-side" arrangement (e.g., the outer surfaces are couple together). In some embodiments (described in more detail below), it may be desirable to couple the first annular member 202 to the second annular member 220 in a "nested" arrangement (e.g., with one annular member being coupled at least partially inside the other).

With continued reference to the embodiment of FIG. 2(b), a flexible mesh structure 240 is coupled to an outer surface of a distal portion 210 of the first annular member 202. An actuating element 250 is coupled to the flexible mesh structure 240. As shown, the actuating element 250 extends from the mesh structure 240 to the proximal portion 228 of the second annular member 220. The actuating element 250 is adapted to deploy the flexible mesh structure 240 to an expanded configuration. As discussed above with reference to the embodiment of FIG. 1, the mesh structure 240 may be deployed to an expanded configuration in response to movement of the actuating element 250, or in response to a signal communicated to the actuating element 250, according to some embodiments.

Figure 2C:
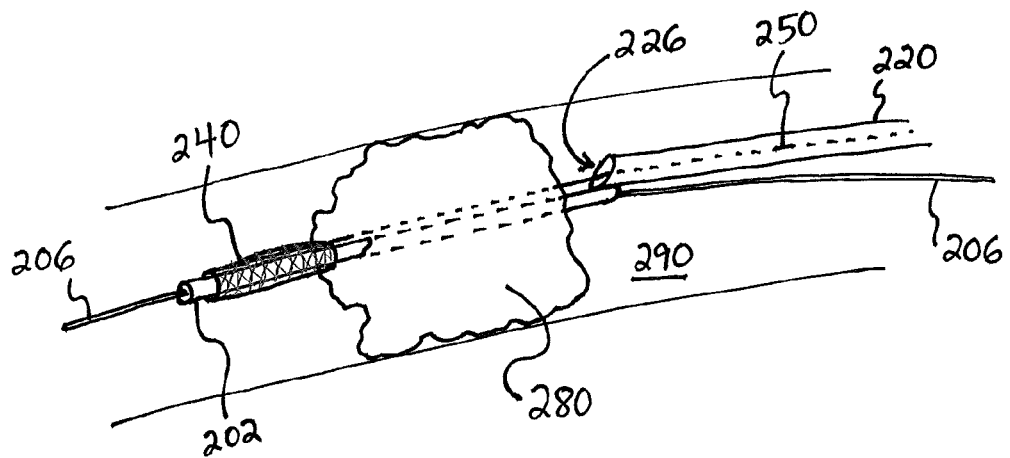

A method of removing a thrombus from a vascular structure is further illustrated in FIG. 2(c). The method may further comprise advancing the thrombus removal device 200 such that the first annular member 202 moves along the guidewire 206 until the flexible mesh structure 240 is positioned distally of the thrombus.

Figure 2D:
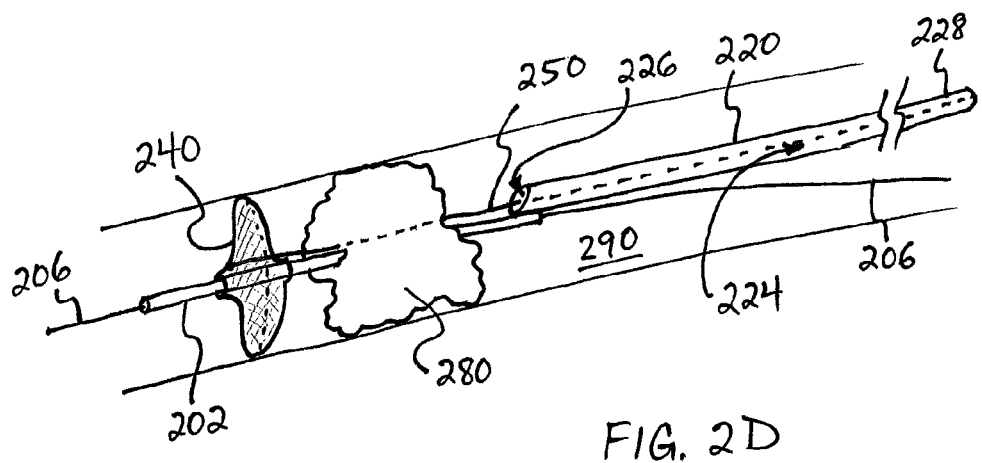

FIG. 2(d) illustrates moving the actuating element 250 to deploy the flexible mesh structure 240 to an expanded configuration. In the expanded configuration, flexible mesh structure 240 may provide distal embolic protection. For example, mesh structure 240 may catch any thrombus or clot material that becomes dislodged and flows in a downstream direction, and prevent such dislodged clot material from causing an embolism.

FIG. 2(d) also illustrates applying a suction force to the suction flow path 224. This may be accomplished, for example, via the proximal portion 228 of the second annular member 220. For example, a syringe (not shown) could be coupled to the proximal portion 228 of the second annular member 220 to create the suction force (e.g., by retracting a plunger of such a syringe). As another example, a vacuum source could be coupled to the proximal portion 228 and selectively applied to the suction flow path 224 to create the suction force.

Figure 2E:
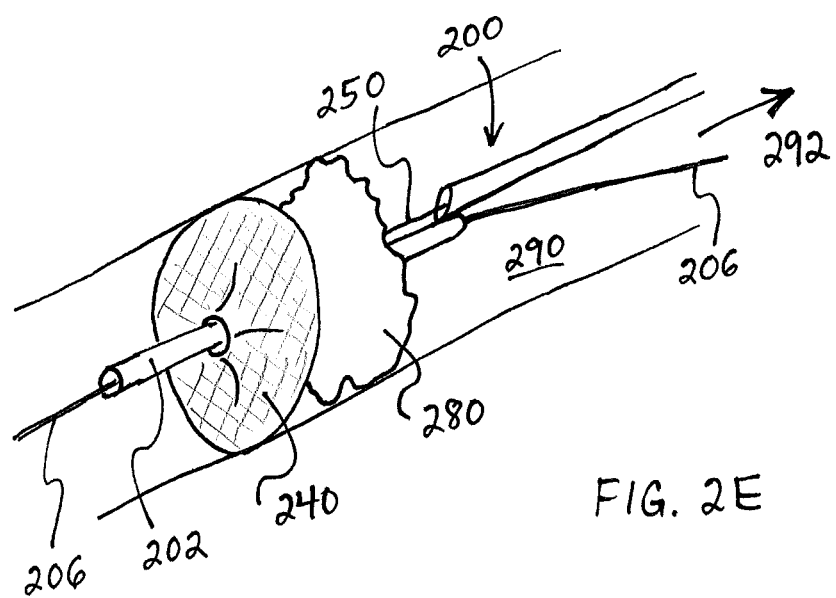

FIG. 2(e) illustrates retracting the thrombus removal device 200 (e.g., moving device 200 proximally, as indicated by arrow 292) such that the flexible mesh structure 240 engages the thrombus 280. As the flexible mesh structure 240 contacts the thrombus 280, the thrombus 280 tends to cling or stick to the flexible mesh structure 240, allowing the thrombus to be pulled (and ultimately, removed) from the vascular structure of interest 290.

FIG. 3(a) is a flowchart showing the above-described steps of a method for removing a thrombus from a vascular structure of interest. Step 301, for example, is to position a guidewire in a vascular structure of interest. Step 302, for example, is to slidably engage the guidewire within a guidewire lumen of a thrombus removal device. For example, a distal end of the guidewire lumen of the thrombus removal device may be positioned to receive the proximal end of the guidewire. Step 303, for example, is to advance the thrombus removal device over the guidewire until a mesh structure of the device is positioned in the vascular structure distal of the thrombus location. Step 304, for example, is to deploy the mesh structure to an expanded configuration via an actuating element of the thrombus removal device. Step 305, for example, is to apply a suction force to a suction flow path (or aspiration flow path) of the device. Step 306, for example, is to retract the device via the guidewire to engage the thrombus with the mesh structure. During step 306, for example, portions of the thrombus may be removed from the vascular structure by a "wiping" action of the mesh structure along a wall of the vascular structure while the device is being retracted. Thus, in some preferred embodiments of the invention, thrombus removal is accomplished by a combination of distal embolic protection (provided by deployment of the mesh structure distal of the thrombus), suction (aspiration) of any dislodged thrombus particles, and wiping or scraping of the thrombus from the wall of the vascular structure with the mesh structure during retraction of the device.

Figure 3B:
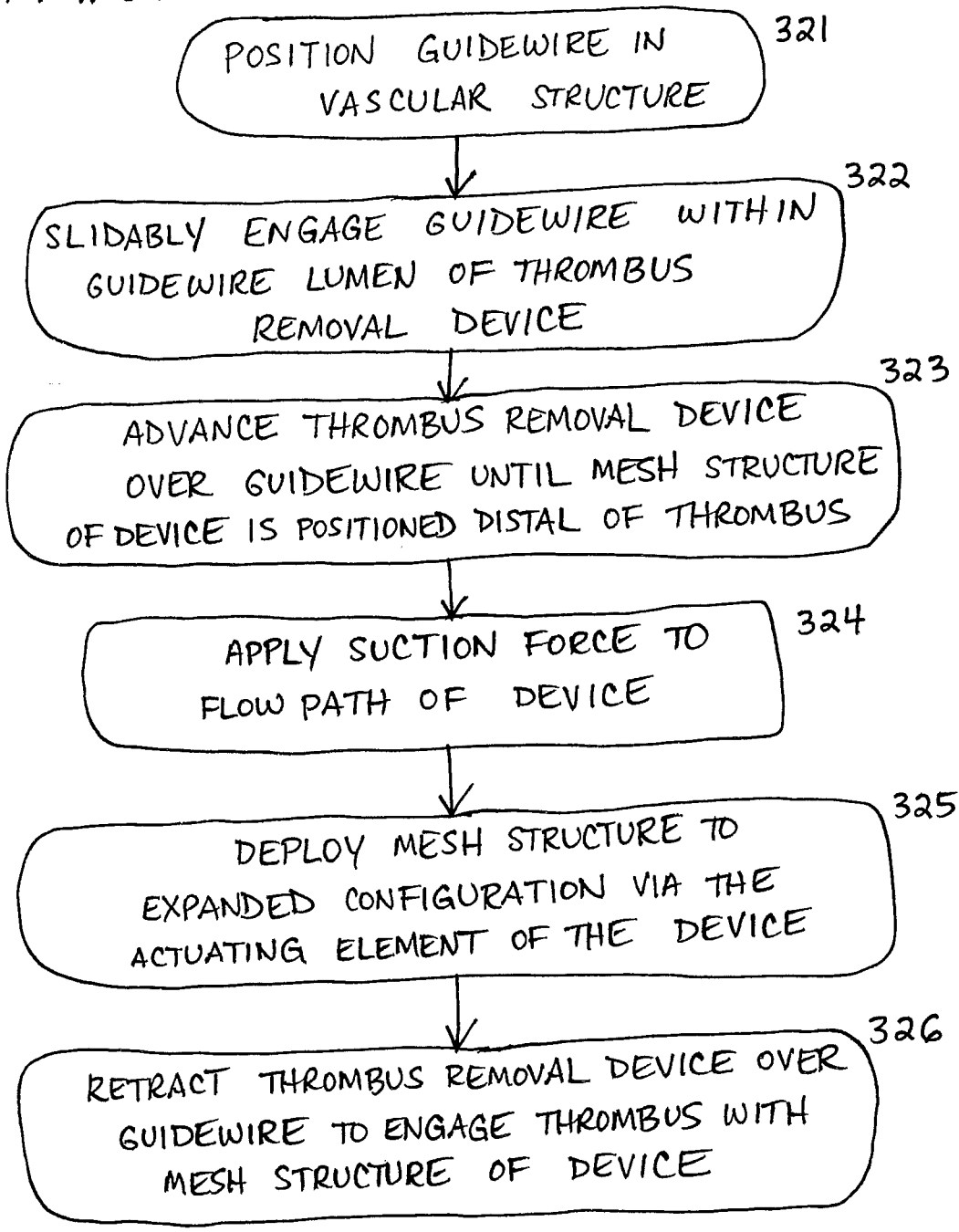

FIG. 3(b) is a flowchart showing an alternate embodiment in which the order of certain steps may be changed from that described above. For example, in the embodiment of FIG. 3(b), the suction force may be applied before the flexible mesh structure is deployed to an expanded configuration. In some embodiments, it may be desirable to apply the suction force even earlier in the method, for example, while advancing the device over the guidewire into the vascular structure of interest. Referring to FIG. 3(b), Step 321, for example, is to position a guidewire in a vascular structure of interest. Step 322, for example, is to slidably engage the guidewire within a guidewire lumen of a thrombus removal device. For example, a distal end of the guidewire lumen of the thrombus removal device may be positioned to receive the proximal end of the guidewire. Step 323, for example, is to advance the thrombus removal device over the guidewire until a mesh structure of the device is positioned in the vascular structure distal of the thrombus location. Step 324, for example, is to apply a suction force to a suction flow path of the device. Step 325, for example, is to deploy the mesh structure to an expanded configuration via an actuating element of the thrombus removal device. Step 326, for example, is to retract the device via the guidewire to engage the thrombus with the mesh structure. During step 326, for example, portions of the thrombus may be removed from the vascular structure by a "wiping" action of the mesh structure along a wall of the vascular structure while the device is being retracted. Thus, in some preferred embodiments of the invention, thrombus removal is accomplished by a combination of distal embolic protection (provided by deployment of the mesh structure distal of the thrombus), suction (aspiration) of any dislodged thrombus particles, and wiping or scraping of the thrombus from the wall of the vascular structure with the mesh structure during retraction of the device.

Figure 4D:
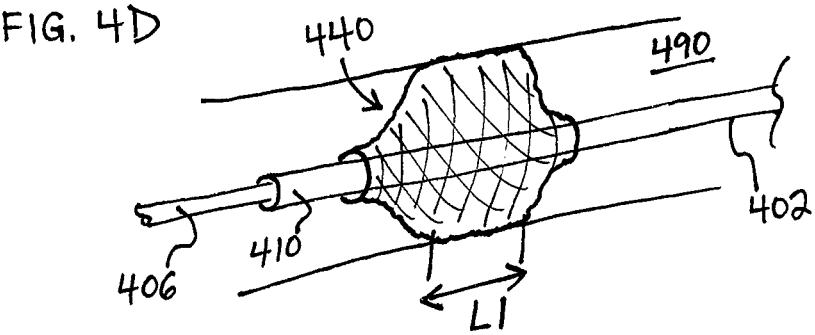

FIG. 4(a) is a partial perspective view of a flexible mesh structure 440 for a thrombus removal device in accordance with certain embodiments. FIG. 4(a) shows a distal portion 410 of a first annular member 402 having a guidewire 406 slidably received therethrough. In the embodiment shown, mesh structure 440 is coupled to an outer surface of distal portion 410. Mesh structure 440 may be of a substantially annular construction, and may substantially conform to the outer surface of distal portion 410 when in an unexpanded (or collapsed) configuration, as shown in FIG. 4(a).

In some embodiments, mesh structure 440 may be formed of a shape memory alloy, such as Nitinol (nickel titanium alloy). In some embodiments, mesh structure 440 may be formed of a titanium mesh. The mesh pattern forms a surface that tends to attract the thrombus and hold it to the mesh. In some embodiments, the mesh pattern is porous enough to allow blood to flow through with little resistance, while blocking or capturing clot particles of a clinically significant size. For example, in some embodiments, openings in the mesh pattern will be large enough to allow blood to pass through easily, while capturing and retaining thrombus (clot) particles that are larger than a specified minimum particle size of about 70-100 microns (and in some preferred embodiments, about 80 microns) in diameter. It should be noted that it may be possible for openings in the mesh pattern to be somewhat larger than the minimum particle size while still capturing the particles due to the tendency of such clot particles to stick together in clumps or strings or chains. For example, it may be a desirable trade-off to have a somewhat larger mesh spacing in order to preserve adequate blood flow through the mesh structure 440, according to certain embodiments.

In some embodiments, mesh structure 440 may comprise a certain amount of radiopaque material within the mesh so that deployment of mesh structure 440 to an expanded configuration may be visually verified using fluoroscopy. This may be accomplished, for example, by forming the mesh with a certain amount of platinum wires, or gold wires, or other radiopaque wire elements within the mesh structure. Such a radiopaque feature may enhance a clinician's ability to confirm that the mesh structure 440 has been properly deployed to the expanded configuration.

Mesh structure 440 may be substantially annular in some embodiments, and may have a proximal end portion 442, a distal end portion 444, and a middle portion 446, the middle portion 446 being adapted to expand radially outwardly when the proximal and distal end portions 442, 444 are positioned more closely together (e.g., one or both ends are moved toward the other), as shown in FIGS. 4(b) and 4(c). For example, FIG. 4(b) shows an embodiment in which the distal portion 444 of the mesh structure 440 is moved proximally via actuating element 450 (in the direction denoted as "D1" in FIG. 4(b)), while the proximal portion 442 is held in place relative to the first annular member 402, in order to deploy the mesh structure 440 from an unexpanded configuration to a radially expanded configuration. For example, in the embodiment shown in FIG. 4(b), the proximal portion 442 of the mesh structure 440 may be connected to the first annular member 402, and the distal portion 444 of the mesh structure 440 may be slidably coupled to the first annular member 402. In such an embodiment, the actuating element 450 may be coupled to the distal portion 444 of mesh structure 440. Alternately, FIG. 4(c) shows an embodiment in which the proximal portion 442 of the mesh structure 440 is slidably coupled to the first annular member 402, and is moved distally via actuating element 450 (in the direction denoted as "D2" in FIG. 4(c)), while the distal portion 444 is held in place relative to the first annular member 402 (e.g., connected to the first annular member 402), in order to deploy the mesh structure 440 from an unexpanded configuration to an expanded configuration. In the unexpanded configuration, shown in FIG. 4(a), the middle portion 446 of mesh structure 440 may be adapted to substantially conform to the first annular member 402, for example, when the proximal and distal end portions 442, 444 are moved away from each other.

Figure 4E:
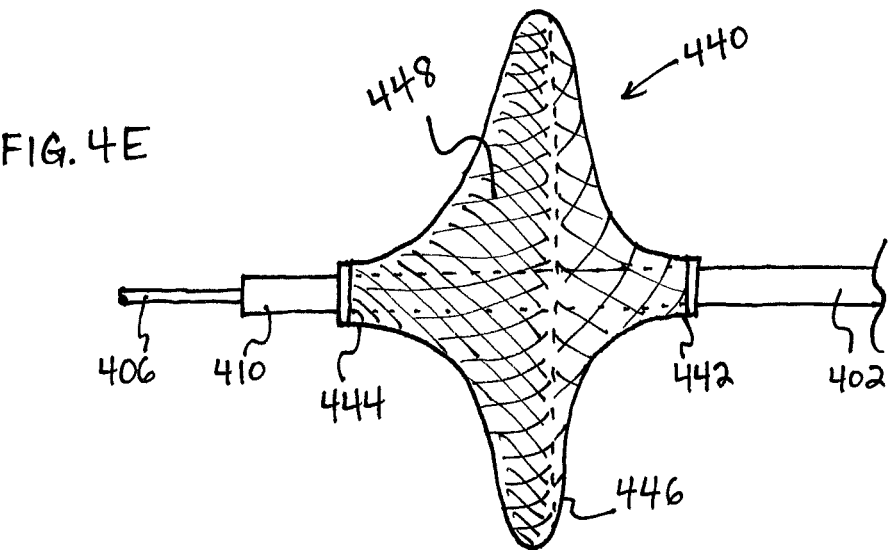
Figure 4F:
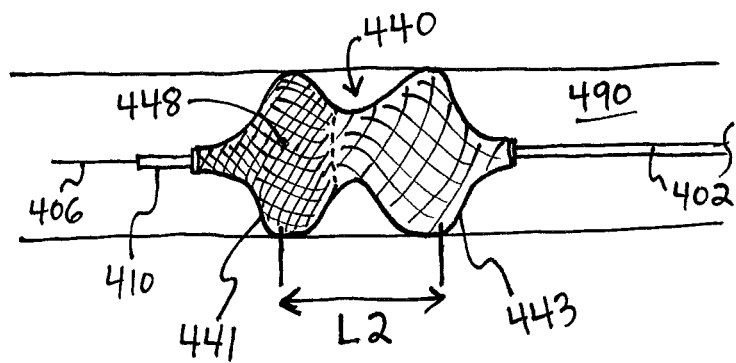

In some embodiments, the expanded configuration of mesh structure 440 should result in the mesh structure becoming large enough (e.g., radially outwardly expanded enough, or wide enough) to substantially cover or substantially span a cross-section of the vascular structure of interest (e.g., an arterial lumen cross-section). In some embodiments, it may be desirable for the mesh structure 440 to provide adequate cross-sectional coverage over a specified minimum length of the vascular structure 490, for example, as shown in FIG. 4(*d*). FIG. 4(*d*) shows a mesh structure 440 in an expanded configuration that covers the vascular cross section along a length, "L1." "L1" may be chosen to be long enough to maintain positive contact across the vessel, while withstanding the forces that may arise when moving the mesh structure 440 (e.g., while "wiping" the clot from the vascular structure). In some embodiments, length "L1" may range from about 1 mm to about 5 mm.

FIG. 4(*e*) shows a mesh structure 440 wherein a denser mesh pattern 448 is employed over a portion of the mesh structure 440, for example, near the distal end of the mesh structure 440. In the embodiment of FIG. 4(*e*), the denser mesh patter 448 exists on a downstream portion of mesh structure 440, including the distal portion 444 and/or part of the middle portion 446. This may provide a higher degree of embolic protection, according to certain embodiments.

FIG. 4(*f*) shows a possible embodiment of a mesh structure 440. In embodiments where a shape memory alloy (such as Nitinol) is used to form mesh structure 440, it may be possible to obtain a variety of shapes that may facilitate the removal of a thrombus from a vascular structure 490. In the embodiment of FIG. 4(*f*), mesh structure 440 has two radially expanded portions 441 and 443 which achieve a desired degree of cross-sectional coverage in the vascular structure. The spacing of such radially expanded portions 441 and 443, denoted as "L2" in FIG. 4(*f*), may also be chosen to facilitate thrombus removal. For example, the expanded portions may be spaced apart from about 2 mm to about 7 mm, according to some embodiments. As also shown, it may be possible to incorporate a denser mesh pattern 448 over a portion of the mesh structure 440, for example, over most of portion 441 in the embodiment of FIG. 4(*f*).

Figure 5A:
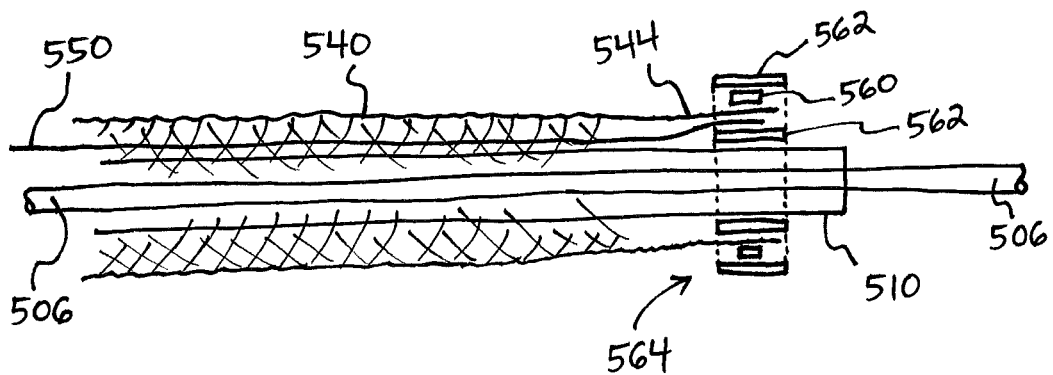
FIGS. 5(a) and 5(b) are cross-sectional side views illustrating a portion of a mesh structure slidably coupled to an outer surface of a first annular member of a thrombus removal device, according to some embodiments.
Figure 5B:
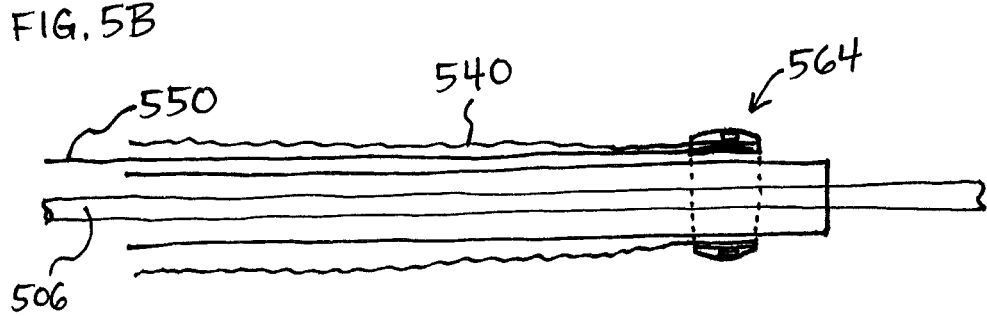

FIG. 5(*a*) is a side view of mesh structure 540 coupled to an outer surface of distal portion 510 of a first annular member of a thrombus removal device, according to certain embodiments. As shown, a collar or slider 564 may be formed at one end (either the proximal or distal end) of the mesh structure 540 to allow the end 544 of the mesh structure 540 to be slidably moved with respect to the first annular member.

In some embodiments, mesh structure 540 may comprise a slider 564 formed at the distal end of mesh structure 540, wherein slider 564 is adapted to move relative to (e.g., slide over) the distal portion of the first annular member. In some embodiments, actuating element 550 may be coupled to slider 564 to effectuate movement of slider 564 (and hence, the distal end of mesh structure 540) relative to the distal portion of the first annular member. In some alternate embodiments, the distal end of the mesh structure 540 may be connected to the first annular member, and the proximal end of the mesh structure 540 may be slidably coupled to the first annular member (e.g., via a slider 564).

Slider 564 may be formed in a number of ways. For example, mesh structure 540 may be crimped and/or folded back on itself at the end 544 of the mesh structure 540 to form a "ring" that can slide relative to an outer surface of the first annular member, thereby forming slider 564. Alternately, mesh structure 540 may be attached to a separate ring-shaped member that forms slider 564. In the particular embodiment shown in FIG. 5(*a*), slider 564 is formed using two polymer layers 562 in a ring-shaped configuration at an end 544 of mesh structure 540, with the end of mesh structure 540 being sandwiched between the two polymer layers 562.

In some embodiments, the two polymer layers 562 may comprise substantially concentric polymer rings that, when treated (e.g., heated), may shrink and/or fuse together, securing the end of mesh structure 540 therebetween. In the specific embodiment illustrated in FIG. 5(*a*), a distal end of actuating element 550 may also be placed between the two polymer layers 562 (with the end of mesh structure 540) prior to being treated (e.g., heated). This may allow actuating element 550, when moved for example, to move the affected end of mesh structure 540 so as to deploy mesh structure 540 to an expanded configuration. In a further embodiment, a radiopaque marker 560 may also be sandwiched between the two polymer layers 562 to provide an indication of the location of the thrombus removal device under x-ray imaging, for example.

FIG. 5(*b*) is a side view of the embodiment described above with respect to FIG. 5(*a*) after slider 564 has been appropriately treated (e.g., heat treated). For example, in the embodiment shown in FIG. 5(*b*), polymer layers 562 have been thermally treated (e.g., heated) to cause the polymer layers 562 to shrink and/or adhere together with the distal end of the mesh structure 540 secured in place between the two polymer layers 562 as a result. In the particular embodiment shown in FIG. 5(*b*), the actuating element 550 and a radiopaque marker 560 may also be secured in place between the two polymer layers 562 as a result of the thermal treating (e.g., heating) process. Radiopaque marker 560 may comprise a thin ring of platinum, for example, according to some embodiments. Actuating element 550 may comprise a metallic wire, for example, according to some embodiments.

FIG. 6(*a*) is a side view of a thrombus removal device 600 showing one possible coupling arrangement of the first annular member 602 and the second annular member 620. In this embodiment, the first annular member 602 is coupled to an outer surface of the second annular member 620, the first annular member 602 being disposed at a distal portion of the second annular member 620. As shown, first annular member 602 is adapted to slidably receive guidewire 606 in a guidewire lumen formed within first annular member 602. Mesh structure 640 is coupled to an outer surface of first annular member 602 and is shown deployed to an expanded configuration in FIG. 6(*a*). Actuating element 650 may be used to deploy mesh structure 640 to the expanded configuration, for example, by pulling actuating element 650 of the embodiment shown in FIG. 6(*a*). Actuating element 650 may be housed substantially within second annular member 620. For example, actuating element 650 may be disposed within a suction flow path 624 (which may also be referred to herein as aspiration lumen 624) of second annular member 620. In the embodiment shown, second annular member 620 has a suction port 626 at a distal end thereof. For example, suction port 626 may comprise an opening in a distal end of the second annular member 620, for example, as shown in FIG. 6(*a*). Suction port 626 may facilitate the removal of any thrombus particles dislodged (e.g., by structure 640) by causing any such dislodged particles to be drawn into suction port 626 and carried away via aspiration lumen 624, according to some embodiments.

FIG. 6(*b*) is a side view of a thrombus removal device 600 showing another possible coupling arrangement of the first annular member 602 and the second annular member 620. In this embodiment, the first annular member 602 is coupled to an inner surface of the second annular member 620, the first annular member 602 being disposed at a distal portion of the second annular member 620. In some embodiments, a portion of an outer surface of the first annular member 602 is coupled directly to an inner surface of the second annular member 620. In some embodiments, the first annular member 602 is coupled to the second annular member 620 in a substantially parallel arrangement. In some embodiments, the first annular member 602 may be arranged to be substantially concentric within the second annular member 620.

As shown in FIG. 6(b), first annular member 602 is adapted to slidably receive guidewire 606 in a guidewire lumen formed within first annular member 602. Mesh structure 640 is coupled to an outer surface of first annular member 602 and is shown deployed to an expanded configuration in FIG. 6(b). The embodiment shown in FIG. 6(b) includes a guidewire port 628 formed in a sidewall of second annular member 620 to allow slidable movement of guidewire 606 therethrough.

With continued reference to FIG. 6(b), an actuating element 650 may be used to deploy mesh structure 640 to the expanded configuration, for example, by pulling actuating element 650 of the embodiment shown in FIG. 6(b). Actuating element 650 may be housed substantially within second annular member 620. For example, actuating element 650 may be housed substantially within a suction flow path 624 (which may also be referred to herein as aspiration lumen 624) of second annular member 620. In the embodiment shown in FIG. 6(b), second annular member 620 has one or more suction ports 626 formed near a distal portion of second annular member 620. For example, the suction port 626 formed at the far distal end of second annular member 620 may be formed at an angle as shown, which may create a larger cross-sectional area for capturing any dislodged thrombus particles. In some embodiments, suction port (or ports) 626 may comprise one or more openings in the sidewall of second annular member 620 near a distal portion thereof, substantially as shown in FIG. 6(b); these could exist in place of, or in addition to, the suction port 626 formed at the far distal end of second annular member 620. The one or more suction ports 626 may facilitate the removal of any thrombus particles dislodged (e.g., by structure 640) by causing any such dislodged particles to be drawn into the suction ports 626 and carried away via aspiration lumen 624, according to some embodiments. The one or more suction ports 626 formed in the sidewall of second annular member 620 may be oval-shaped according to some embodiments; this may yield greater structural strength for a given opening size, for example. Preferably, such oval-shaped suction ports 626 in the sidewall of second annular member 620 would have their longer axis substantially aligned with the longitudinal axis of the second annular member 620, substantially as shown in FIGS. 6(b)-(c).

First annular member 602 may be formed of any suitable material known in the art. First annular member 602 may be formed of flexible tubing, for example. In some embodiments, first annular member 602 may comprise a polyimide tube. In some embodiments, first annular member 602 may be between about 5 and 30 centimeters in length. As previously noted, first annular member 602 is adapted to slidably receive a guidewire 606 in a guidewire lumen formed within first annular member 602. This arrangement of the first annular member 602, guidewire 606, and second annular member 620 may sometimes be referred to as a "monorail" configuration. A monorail configuration may, for example, provide a benefit to a user of device 600 by allowing the length of the device that is actually in contact with guidewire 606 to be minimized. This may, for example, improve the handling characteristics of device 600 and/or make it more convenient to use.

FIG. 6(c) shows a slight modification of the embodiment shown in FIG. 6(b) wherein the proximal end of first annular member 602 extends proximally of guidewire port 628. Guidewire port 628 in such an embodiment may extend through a sidewall of second annular member 620 and through a sidewall of first annular member 602 to allow slidable movement of guidewire 606 through both structures.

Figure 6D:
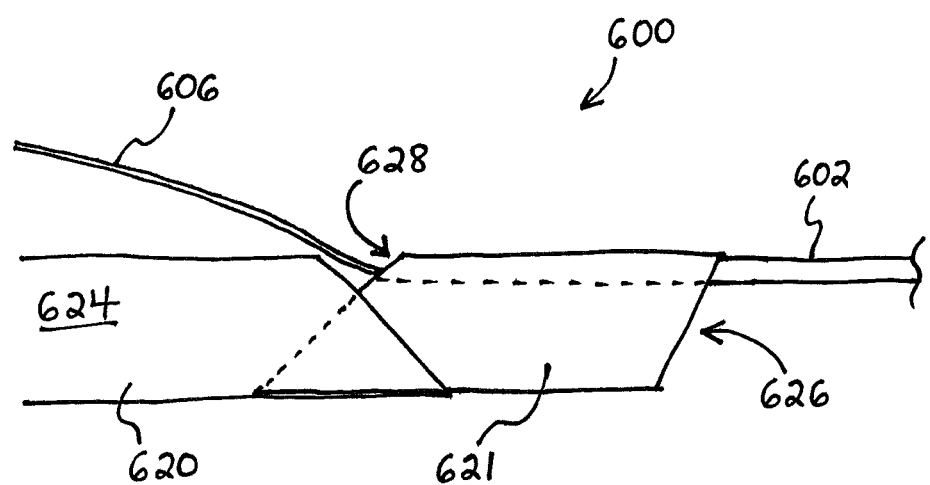

FIG. 6(d) is a partial side view of an alternate embodiment of device 600. In this particular embodiment, second annular member 620 is effectively extended via extension 621. For example, the distal end of second annular member 620 may be cut at an angle as shown. Similarly, extension 621 may cut at an angle at its proximal end. Extension 621 and second annular member 620 may then be coupled together in an overlapping manner (e.g., one partially nested within the other) such that a gap remains to form guidewire port 628. Similar arrangements and variations thereof are contemplated for providing guidewire port 628, and are deemed to be within the scope of the claims appended hereto.

FIG. 7 is a side view of thrombus removal device 700 according to some embodiments. In the embodiment shown, second annular member 720 has a proximal portion 728 adapted to couple device 700 to a suction source and/or an actuating mechanism. For example, proximal portion 728 may comprise a suction source coupling or connection 760, which may be a port (e.g., a luer fitting) for coupling a suction source (not shown) to the suction flow path 724. For example, connection 760 may allow suction flow path 724 to be fluidly coupled to an external source of suction (e.g., negative pressure), such as a syringe (e.g., in which the plunger may be withdrawn to create a suction force) or a vacuum source (e.g., a source of suction that may be selectively applied and controlled, for example, via valving).

Proximal portion 728 may include a handle 770 adapted to cause actuating element 750 to move in an axial direction. Handle 770 may comprise a knob or gripping surface that allows a user to move actuating element 750 axially (e.g., proximally and/or distally by pushing and/or pulling) in some embodiments. In some embodiments, handle 770 may incorporate a biasing force, such as a spring 772, which allows a user to move actuating element 750 by moving handle 770 in opposition to the biasing force, for example. A "trigger"-style embodiment, in which a user pulls back on a trigger against the force of a spring would be one possible example of such an embodiment that would be apparent to one of ordinary skill in the art with the benefit of these teachings. Handle 770 may alternately (or additionally) incorporate a rotating element, which may allow precise control of the movement of actuating element 750. For example, rotation of handle 770 may cause axial movement of actuating element 750 due to screw-type threads 774 in the proximal portion 728, as would be known to one of ordinary skill in the art. For example, rotation of the handle 770 may cause the actuating element 750 to move longitudinally, either distally or proximally, depending on the direction of rotation of handle 770. It may also be desirable in some embodiments to incorporate a locking mechanism 776 into proximal portion 728 and/or handle 770 to hold actuating element 750 stationary, and thereby maintain a deployed or non-deployed configuration (e.g., either an expanded configuration or an unexpanded configuration) of mesh structure 740 once the actuating element 750 has been moved to achieve the desired configuration by a user.

With continued reference to FIG. 7, second annular member 720 may be formed of a variety of suitable materials. In some embodiments, second annular member 720 may be adapted to advance the first annular member 702 over the guidewire 706 to position the flexible mesh structure 740 near a thrombus (for example, by enabling the first annular member 702 to be "pushed" into a vascular structure of interest using the second annular member 720). This is typically accomplished by an operator first inserting a "standard" medical guidewire 706 into a vasculature structure of interest and advancing it past the thrombus. The device 700 may then be deployed, for example, by "threading" the first annular member 702 onto the guidewire 706 such that the guidewire lumen of the first annular member 702 slides over the guidewire 706, then advancing the first annular member 702 (and the mesh structure 740) by moving (e.g., pushing and/or pulling) the second annular member 720 until the mesh structure 740 is positioned distal of the thrombus.

Second annular member 720 may be formed of a thermoplastic elastomer such as Pebax®, or nylon-12, for example. Polyimide is another example of a material that may be suitable for forming second annular member 720 (e.g., polyimide tubing). In some embodiments, it may be desirable for the durometer (a measure of the "hardness" of a material) of second annular member 720 to vary over its length. For example, in one specific embodiment, a Shore A durometer of 62 was used in a distal portion 722 of second annular member 720, and a Shore A durometer of 72 was used in part of the middle portion and/or the proximal portion 728 of the second annular member 720 to achieve a desired balance of stiffness and flexibility. In some embodiments, the second annular member 720 is between about 40 and 200 centimeters in length.

The present disclosure has described a number of exemplary embodiments and some preferred embodiments and implementations, by way of example only. It will be understood by those having ordinary skill in the pertinent fields that modifications to any of the embodiments or preferred embodiments may be easily made without materially departing from the scope of the present disclosure, as defined by the appended claims.

What is claimed is:

1. A device for removing a thrombus from a vascular structure, the device comprising:
a first annular member having a guidewire lumen for slidably receiving a guidewire;
a second annular member coupled to the first annular member, the second annular member adapted to provide a suction flow path from a suction port in a distal portion of the second annular member to a proximal portion of the second annular member, the distal portion of the second annular member being directly coupled to a proximal portion of the first annular member;
a flexible mesh structure coupled to an outer surface of a distal portion of the first annular member,
the suction port of the second annular member positioned to be in direct fluid communication with the vascular structure proximal of the flexible mesh structure, a longitudinal axis of the second annular member intersecting the suction port, and
an actuating element coupled to the flexible mesh structure, the actuating element extending externally of the first annular member from the mesh structure to the distal portion of the second annular member and extending on to the proximal portion of the second annular member, the actuating element adapted to deploy the flexible mesh structure to an expanded configuration in response to movement of the actuating element with respect to the second annular member.

2. The device of claim 1 wherein the flexible mesh structure comprises a nitinol mesh.

3. The device of claim 1 wherein the flexible mesh structure has a mesh pattern which can capture particles of a clinically significant size.

4. The device of claim 3 wherein the flexible mesh structure has a denser mesh pattern near a distal end of the mesh structure.

5. The device of claim 1 wherein the flexible mesh structure is substantially annular, having a proximal end, a distal end, and a middle portion, the middle portion being adapted to expand radially outward to the expanded configuration when the proximal and distal ends are positioned more closely together.

6. The device of claim 5 wherein the middle portion of the mesh structure is adapted to conform to the first annular member when the flexible mesh structure is in an unexpanded configuration.

7. The device of claim 5 wherein the proximal end of the mesh structure is connected to the first annular member, and the distal end of the mesh structure is slidably coupled to the first annular member.

8. The device of claim 7 wherein the actuating element is coupled to the distal end of the mesh structure.

9. The device of claim 7 wherein the mesh structure further comprises a slider at the distal end of the mesh structure, the slider adapted to slide over the distal portion of the first annular member.

10. The device of claim 9 wherein the actuating element is coupled to the slider.

11. The device of claim 5 wherein the distal end of the mesh structure is connected to the first annular member, and the proximal end of the mesh structure is slidably coupled to the first annular member.

12. The device of claim 1 wherein the suction port comprises an opening in a distal end of the second annular member.

13. The device of claim 1 further comprising one or more openings in a sidewall of the distal portion of the second annular member.

14. The device of claim 1 wherein the second annular member is adapted to advance the first annular member over the guidewire to position the flexible mesh structure near a thrombus.

15. The device of claim 1 wherein the proximal portion of the second annular member comprises a connection for coupling a suction source to the suction flow path.

16. The device of claim 15 wherein the suction source comprises a syringe.

17. The device of claim 15 wherein the suction source comprises a vacuum.

18. The device of claim 1 wherein the proximal portion of the second annular member comprises a handle for moving the actuating element.

19. The device of claim 18 wherein the handle is adapted to rotate to move the actuating element longitudinally.

20. The device of claim 18 wherein the handle further comprises a locking mechanism adapted to maintain the mesh structure in either an expanded configuration or an unexpanded configuration.

21. The device of claim 18 wherein the handle is adapted to move the actuating element proximally or distally.

22. The device of claim 21 wherein the handle comprises a spring-loaded trigger.

23. The device of claim 1 wherein the second annular member comprises a polyimide tube.

24. The device of claim 1 wherein the second annular member is formed of a thermoplastic elastomer.

25. The device of claim 24 wherein the second annular member is formed of nylon-12.

26. The device of claim 1 wherein the second annular member is between about 40 and 200 centimeters in length.

27. The device of claim 1 wherein the first annular member comprises a polyimide tube.

28. The device of claim 1 wherein the first annular member is between about 5 and 30 centimeters in length.

29. The device of claim 1 wherein the first annular member is coupled to the second annular member in a substantially parallel arrangement.

30. The device of claim 29 wherein the first annular member is coupled to an outer surface of the second annular member.

31. The device of claim 29 wherein the first annular member is coupled to an inner surface of the second annular member.

32. The device of claim 31 wherein the first annular member is substantially concentric within the second annular member.

33. The device of claim 31 wherein an outer surface of the first annular member is coupled directly to an inner surface of the second annular member.

34. The device of claim 1 wherein the actuating element is disposed within the suction flow path.

* * * * *